United States Patent [19]

Bock et al.

[11] 4,309,430

[45] Jan. 5, 1982

[54] PYRAZINYL-1,2,4-OXADIAZOLE-5-ONES, FOR TREATMENT OF EDEMA, AND PROCESSES FOR PREPARING SAME

[75] Inventors: Mark G. Bock, Hatfield; Robert L. Smith, Lansdale, both of Pa.

[73] Assignee: Merck & Co., Inc., Rahway, N.J.

[21] Appl. No.: 163,614

[22] Filed: Jun. 27, 1980

[51] Int. Cl.³ .................... A61K 31/54; A61K 31/42; C07D 241/08
[52] U.S. Cl. .................................. 424/250; 424/246; 544/405; 548/132
[58] Field of Search ..................... 544/405; 548/132; 424/250

[56] References Cited

U.S. PATENT DOCUMENTS 3,770,739  11/1973  Fanshawe et al. ................ 544/405

OTHER PUBLICATIONS

Falck, "Ber," vol. 18, (1885), pp. 2467–2476.
Iwao et al., "J. Hetero. Chem.," vol. 14 (1977), pp. 993–996.
Goodman et al., "The Phamacological Basis of Therapeutics," 6th ed, pp. 911–912.

*Primary Examiner*—Anton H. Sutto
*Attorney, Agent, or Firm*—Raymond M. Speer; Michael C. Sudol

[57] ABSTRACT

The case concerns novel pyrazinyl-1,2,4-oxadiazole-5-ones and processes for preparing the same. The compounds are useful in the treatment of edema and hypertension.

11 Claims, No Drawings

PYRAZINYL-1,2,4-OXADIAZOLE-5-ONES, FOR TREATMENT OF EDEMA, AND PROCESSES FOR PREPARING SAME

SUMMARY OF THE INVENTION

The novel compounds in this invention are depicted in Formula I.

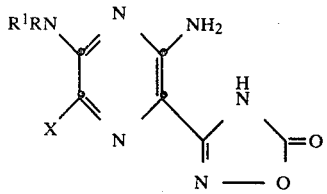

wherein
- R is hydrogen or lower alkyl ($C_{1-5}$) such as methyl, ethyl, isopropyl, n-butyl, n-pentyl;
- $R^1$ is hydrogen or lower alkyl ($C_{1-5}$) such as methyl, ethyl, isopropyl, n-butyl, n-pentyl;
- R and $R^1$ can be joined to form an alkylene group of from 2–4 carbon atoms such as an ethylene or butylene chain, and
- X is halo such as fluoro, chloro, bromo or iodo, cyano or phenyl.

The preferred compounds of this invention are those compounds of Formula I wherein
- R is hydrogen or methyl;
- $R^1$ is hydrogen or methyl;
- X is halo.

Specifically preferred compounds of this invention are 2-($\Delta^2$-1,2,4-oxadiazol-5-one-3-yl)-3,5-diamino-6-chloropyrazine, 2-($\Delta^2$-1,2,4-oxadiazol-5-one-3-yl)-3-amino-5-dimethylamino-6-chloropyrazine, 2-($\Delta^2$-1,2,4-oxadiazol-5-one-3-yl)-3,5-diamino-6-fluoropyrazine, 2-($\Delta^2$-1,2,4-oxadiazol-5-one-3-yl)-3-amino-5-dimethylamino-6-fluoropyrazine.

Compounds of this invention as shown by Formula I are useful because they possess diuretic, naturetic and antikaluretic properties and can be used in the treatment associated with electrolyte imbalance such as in the treatment of edema and associated hypertension. The compounds of this invention are less basic, chemically more stable and more easily manipulated such as during isolation and synthesis than the parent carboxamidine compounds.

The products of this invention can be administered to patients (both human and animal) in the form of pills, tablets, capsules, elixirs, injectable preparations and the like. They can be administered either orally or parentally or any other feasible method as known to those skilled in the art such as intravenously or in the form of suppositories and the like.

The type of formulation to be administered can be comprised of one or more of the compounds of this invention as the only essential active ingredient of the pharmaceutical formulation. The formulations are merely combinations of the active ingredient mentioned with pharmaceutically inert carriers and the like. Several pharmaceutical formulations are prepared as shown in Examples 2 and 3.

The compounds of this invention are advantageously administered at a dosage range of from about 5 mg. to about one gram per day or a somewhat higher or lower dosage at the physician's discretion, preferably in subdivided amounts on a 2 to 4 times a day regimen and most preferably at a dosage range from 10 to 500 mg. per day. It will be realized by those skilled in the art that the dosage range for any particular patient (animal or human) will depend upon the severity of the disease treated, weight of the patient and any other condition which the physician or other person skilled in the art will take account of.

The compounds of this invention can be administered as shown above either alone with the general pharmaceutical carriers or in combination with other kaliuretic diuretics such as, for example in combination with hydrochlorothiazide and the like with pharmaceutical carriers.

Example 3 shows the preparation of a typical combination product. The combination dosage in a typical formulation to be administered as described above is 5–100 mg. of a compound of this invention with 50–100 mg. of a kaluretic diuretic such as hydrochlorothiazide. Generally a good ratio between the two active ingredients is 1 to 10 (compound of this invention to the kaluretic diuretic). The combination products can be administered in similar dosages as that described above for the administration of a single compound of this invention. Again, it will be realized that the dosage range for any particular patient will depend on the severity of the disease being treated, weight of the patient and any other conditions which the physician or other person skilled in the art will take account of.

The compounds disclosed in this invention in Formula I and the preferred compounds can be formed according to one or more of the processes described below.

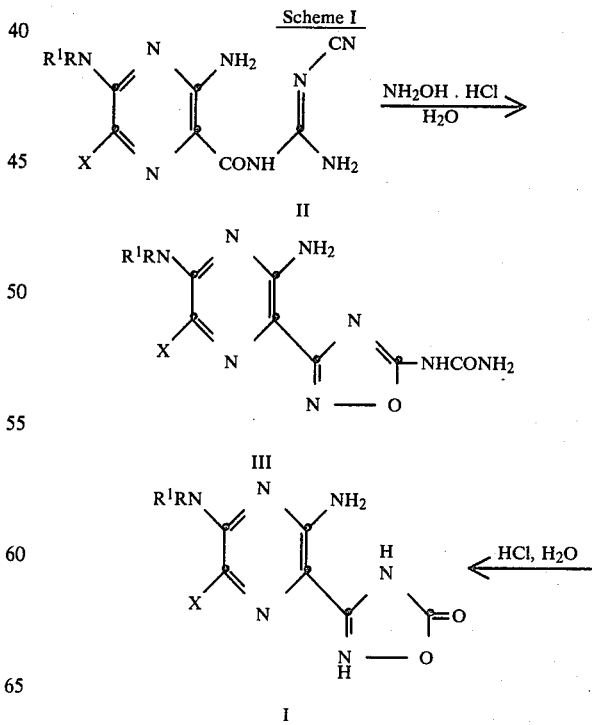

wherein R, $R^1$ and X are as defined in Formula I.

N-(Cyanoaminoiminomethyl)pyrazinecarboxamides II are suspended in water or in another suitable protic solvent like methanol, ethanol or isopropanol and treated with hydroxylamine hydroxchloride. The resulting suspension is rapidly stirred at temperatures ranging from 23° C. to the boiling point of the solvent for 2 to 24 hours. The crude reaction product III is then isolated by filtration and treated further with hot hydrochloric acid solution (preferably at 6 N). The suspension is again filtered and the desired product is obtained by crystallization from the filtrate.

The following examples describe the preparation of certain compounds which are illustrative of the novel compounds of this invention, and certain specific dosage forms suitable for administering the novel compounds. It is to be understood that the invention is not to be limited to the specific compounds described in the example or by the specific reaction conditions described for the preparation of these compounds or by the specific ingredients included in the pharmaceutical preparations, but is to be understood to embrace variations and modifications thereof which fall within the scope of the appended claims.

EXAMPLE 1

Preparation of 2-($\Delta^2$-1,2,4-oxadiazol-5-one-3-yl)-3,5-diamino-6-chloropyrazine To a rapidly stirred suspension of 3,5-diamino-6-chloro-N-(cyanoaminoiminomethyl)pyrazine carboxamide II (16.52 g, 0.0649 mole) in 150 ml of water is added a solution of 25 ml of water containing 4.78 g (0.0687 mole) of hydroxylamine hydrochloride. The resulting suspension is refluxed for 5 hours. The reaction mixture is cooled and filtered. The resulting crude product thus obtained (19.0 g) is suspended in 600 ml of water and treated with 300 ml of concentrated hydrochloric acid. The suspension is heated until the reaction mixture is nearly homogenous, then filtered hot to remove traces of insoluble material. Within 1 hour, an orange-brown precipitate is obtained which is removed by filtration. The filtrate is concentrated to half its volume and then allowed to stand at room temperature. Within several hours the title compound precipitates from solution in analytically pure form (28% yield); mp 300° C., decomp.

Elemental analysis for $C_6H_5N_6O_2Cl$: Calc.: N, 36.77; C, 31.50; H, 2.20; Found: N, 36.87; C, 31.07; H, 2.36.

ir(KBr, partial): 3325, 1750, 1630, 1530, 1435, 1265, 1070 cm$^{-1}$.

Pmr (DMSO-$d_6$): $\delta$7.2 (v.broad exchangeable peak).

$^{13}$Cnmr (DMSO-$d_6$): 105.85, 112.28, 152.15 (2 carbons), 157.03, 158.79 ppm.

UV$_{max}$ (EtOH): 278 nm.

MS: M$^+$228, M-30=198, M-CO$_2$=184, M-CO$_2$NH=169.

EXAMPLE 2

Compressed Tablet containing 50 mg. of active ingredient.

| | Per tablet, Mg. |
|---|---|
| 2-($\Delta^2$-1,2,4-oxadiazol-5-one-3-yl)-3,5-diamino-6-chloropyrazine | 50 |
| Calcium phosphate dibasic | 200 |
| Ethyl cellulose (as 5% solution in ethanol) | 5 |
| Unmixed granulation | 255 |

-continued

| | Per tablet, Mg. |
|---|---|
| Add: | |
| Starch, corn | 14 |
| Magnesium stearate | 1 |
| | 270 |

Directions: Mix the active ingredient above and calcium phosphate and reduce to a No. 60 mesh powder. Granulate with Ethocel in alcohol and pass the wet granulation through a No. 10 screen. Dry the granulation at 110° F. for 12-18 hours. Dry grind to a No. 20 mesh. Incorporate the "adds" and compress into tablets each weighing 270 mg.

EXAMPLE 3

Combination dosage form in dry filled capsule.

| | Per capsule, mg. |
|---|---|
| 2-($\Delta^2$-1,2,4-oxadiazol-5-one-3-yl)-3,5-diamino-6-chloropyrazine | 10 |
| Hydrochlorothiazide | 50 |
| Magnesium stearate | 2 |
| Lactose | 73.5 |
| Mixed powders total | 185.5 |

Mix all of the above ingredients, reduce to a No. 60 mesh powder and encapsulate filling 105.5 mg. in each No. 2 capsule.

What is claimed is:

1. A method of treatment of edema which comprises administering to a patient in need of such treatment a pharmaceutically effective dose of the formula

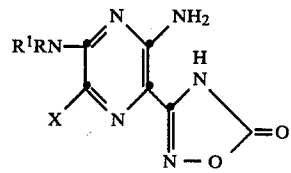

wherein
R is hydrogen or lower alkyl (C$_{1-5}$),
R$^1$ is hydrogen or lower alkyl (C$_{1-5}$),
R and R$^1$ can be joined to form an alkylene group of from 2-4 carbon atoms, and
X is halo, cyano or phenyl.

2. A method for treatment of edema which comprises administering to a patient in need of such treatment a pharmaceutically effective dose of a compound of the formula:

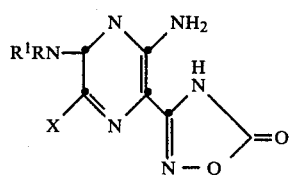

wherein
R is hydrogen or methyl;
R$^1$ is hydrogen or methyl; and
X is halo.

3. A pharmaceutical composition useful in the treatment of edema which comprises a compound of the formula

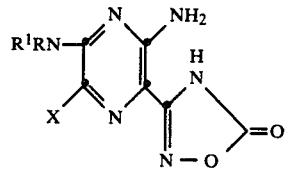

wherein

R is hydrogen or lower alkyl ($C_{1-5}$), $R^1$ is hydrogen or lower alkyl ($C_{1-5}$), R and $R^1$ can be joined to form an alkylene group of from 2–4 carbon atoms, and X is halo, cyano or phenyl.

and a pharmaceutically acceptable carrier.

4. A pharmaceutical composition useful in the treatment of edema which comprises a compound of the formula

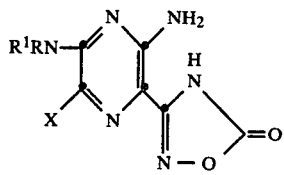

wherein

R is hydrogen or methyl;

$R^1$ is hydrogen or methyl; and

X is halo.

5. A compound of the formula:

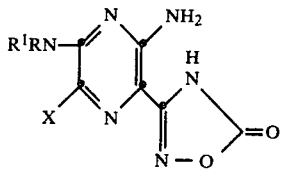

wherein

R is hydrogen or lower alkyl ($C_{1-5}$), $R^1$ is hydrogen or lower alkyl ($C_{1-5}$), R and $R^1$ can be joined to form an alkylene group of from 2–4 carbon atoms, and X is halo, cyano or phenyl.

6. A compound of the formula:

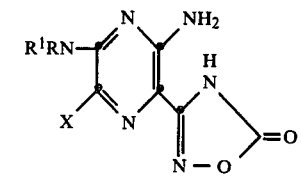

wherein

R is hydrogen or methyl;

$R^1$ is hydrogen or methyl; and

X is halo.

7. A compound of claim 6 wherein R and $R^1$ are hydrogen and X is chloro thus forming 2-($\Delta^2$-1,2,4-oxadiazol-5-one-3-yl)-3,5-diamino-6-chloropyrazine.

8. A compound of claim 6 wherein R and $R^1$ are methyl and X is chloro thus forming 2-($\Delta^2$-1,2,4-oxadiazol-5-one-3-yl)-3-amino-5-dimethylamino-6-chloropyrazine.

9. A compound of claim 6 wherein R and $R^1$ are hydrogen and X is fluoro thus forming 2-($\Delta^2$-1,2,4-oxadiazol-5-one-3-yl)-3,5-diamino-6-fluoropyrazine.

10. A compound of claim 6 wherein R and $R^1$ are methyl and X is fluoro thus forming 2-($\Delta^2$-1,2,4-oxadiazol-5-one-3-yl)-3-amino-5-dimethylamino-6-fluoropyrazine.

11. A process for preparing a compound of the Formula

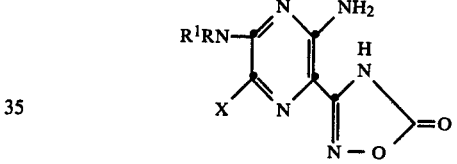

wherein

R is hydrogen or lower alkyl ($C_{1-5}$), $R^1$ is hydrogen or lower alkyl ($C_{1-5}$), R and $R^1$ can be joined to form an alkylene group of from 2–4 carbon atoms, and X is halo, cyano or phenyl which comprises reacting a compound of the formula

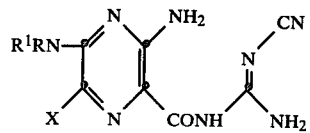

with hydroxylamine hydroxchloride to form an intermediate of the formula

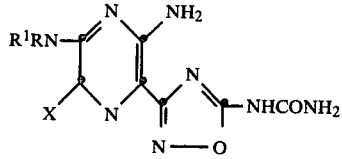

and then reacting said latter compound with a hot hydrochloric acid solution to produce the desired product.

* * * * *